US012070535B2

(12) United States Patent
Chakroun

(10) Patent No.: US 12,070,535 B2
(45) Date of Patent: Aug. 27, 2024

(54) INTELLIGENT SYSTEMS FOR DISPENSING BY NEBULISATION

(71) Applicant: Ilyes Chakroun, La Soukra Ariana (TN)

(72) Inventor: Ilyes Chakroun, La Soukra Ariana (TN)

( * ) Notice: Subject to any disclaimer, the term of this patent is extended or adjusted under 35 U.S.C. 154(b) by 429 days.

(21) Appl. No.: 17/428,743

(22) PCT Filed: Oct. 19, 2020

(86) PCT No.: PCT/IB2020/059799
§ 371 (c)(1),
(2) Date: Aug. 5, 2021

(87) PCT Pub. No.: WO2021/079248
PCT Pub. Date: Apr. 29, 2021

(65) Prior Publication Data

US 2022/0143253 A1 May 12, 2022

(30) Foreign Application Priority Data

Oct. 22, 2019 (FR) ........................................ 1911777

(51) Int. Cl.
*A61L 9/12* (2006.01)
*A61L 9/14* (2006.01)

(52) U.S. Cl.
CPC .................................... *A61L 9/12* (2013.01); *A61L 9/14* (2013.01); *A61L 2209/111* (2013.01)

(58) Field of Classification Search
CPC ........ A61L 9/12; A61L 9/14; A61L 2209/111; A61L 9/125; Y02B 30/70
See application file for complete search history.

(56) References Cited

U.S. PATENT DOCUMENTS 8,490,889 B2 * 7/2013 Rydbom .................... A61L 9/12 239/37
2005/0224596 A1 * 10/2005 Panopoulos .......... A01M 25/00 239/722

(Continued)

FOREIGN PATENT DOCUMENTS

WO 2015/145452 A1 10/2015

OTHER PUBLICATIONS

International Search Report (PCT/ISA/210) mailed on Jan. 22, 2021 for International Application No. PCT/IB2020/059799 (English Translation).

(Continued)

*Primary Examiner* — Donnell A Long
(74) *Attorney, Agent, or Firm* — INNOVATION CAPITAL LAW GROUP, LLP; Vic Lin

(57) ABSTRACT

A system (1-9) for dispensing, in particular by nebulization, a liquid in an environment (10), this system comprising at least one dispensing device (1-4) having a settable operating parameter and configured to dispense said liquid, a plurality of sensors (6-9), a control unit (5) configured to gather a datum captured by at least one sensor of said plurality of sensors (6-9) and to adjust, based on at least said captured datum, said operating parameter of said at least one dispensing device (1-4), said plurality of sensors comprising at least one air quality sensor, this air quality sensor incorporating a suction fan configured to suck air, the air quality sensor being configured to measure the quality of the sucked air.

9 Claims, 1 Drawing Sheet

(56) References Cited

U.S. PATENT DOCUMENTS

| | | | | |
|---|---|---|---|---|
| 2007/0204388 | A1* | 9/2007 | Zyskowski | A61L 9/14 4/228.1 |
| 2018/0290159 | A1* | 10/2018 | Gruenbacher | B41J 29/377 |
| 2019/0061466 | A1 | 2/2019 | MacNeille et al. | |
| 2019/0085852 | A1 | 3/2019 | Brown et al. | |

OTHER PUBLICATIONS

Written Opinion (PCT/ISA/237) mailed on Jan. 22, 2021 for International Application No. PCT/IB2020/059799 (non-English).

* cited by examiner

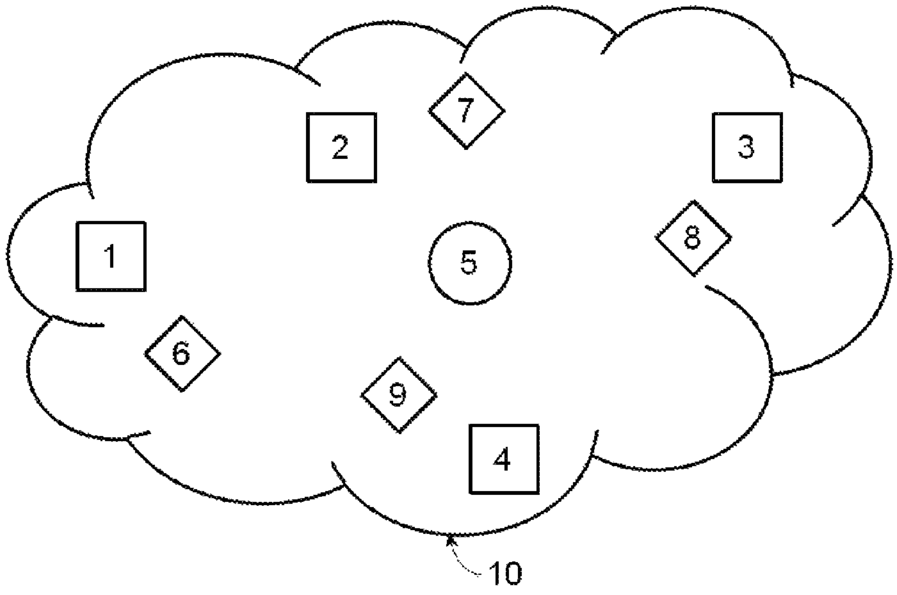
1
2
3
4
5
6
7
8
9
10

INTELLIGENT SYSTEMS FOR DISPENSING BY NEBULISATION

The present invention relates to the technical field of dispensing systems, in particular by nebulization, of a liquid in the atmosphere of an indoor or outdoor environment, and more particularly to the monitoring of the operation of such systems.

There are several techniques for dispensing one or several liquid(s) into the ambient air. Mention may be made of dispensing by atomization, by nebulization, or even by misting. Depending on the used products, this dispensing may aim to treat the ambient atmosphere (odorization/deodorization, disinfection, or sanitation for example), to heal (aromatherapy, dermatology), to fight against pests (disinfection, repulsion), or to improve the comfort of the ambient space (freshness, relaxation, cosmetics, or olfactory marketing, for example).

This dispensing finds application in different environments such as healthcare premises (hospitals, clinics, spa centers), accommodation centers, hotels, banks, living areas, points of sale, shopping centers, beauty centers, cultural premises, business centers, or industrial or agricultural production sites.

Among the dispensing techniques, that by nebulization preserves the properties of the liquid to be dispensed and, thanks to the transformation of this liquid into very fine light particles which can remain in suspension for a long time in the atmosphere, is relatively effective.

Associated with these advantages, solutions for automation and servo-control of the operation of nebulizers have also been proposed. The nebulization time and/or the intensity of this nebulization can indeed be programmed and automatically adjusted according to parameters relating to the dispensing environment such as the temperature, the detection of a predefined odor, or the occupancy rate of this environment. The document US 2019/061466 describes a system for improving the quality of the air inside a vehicle.

Nevertheless, these solutions of the prior art are imperfect, in particular with respect to the relevance of the parameters taken into consideration for monitoring/adapting the operation of the nebulizers. An improper control of a dispensing device can cause overconsumption of the nebulized liquid, an overconcentration of this liquid in the atmosphere or in particular areas thereof, as well as all the consequences that might result for the occupants or, on the contrary, an insufficient yield does not make it possible to achieve a desired result.

One object of the present invention is to remedy the aforementioned drawbacks.

Another object of the present invention is to improve the real-time monitoring of the nebulizers according to parameters relating to the environment which are variable and, possibly, not foreseen in advance by a predefined dispensing program.

Another object of the present invention is to refine the control and to improve the performance of servo-control of the dispensing devices in order to best meet the needs of the users.

Another object of the present invention is to ensure a dispensing by nebulization adapted to the current, or even instantaneous, context in the considered space.

Another object of the present invention is to ensure, in a specific location, a monitored distribution (uniform, multifaceted, homogeneous or heterogeneous for example) of a nebulized gas flow.

Another object of the present invention is to optimize the efficiency of the nebulizers or, more generally, of the dispensing devices.

Another object of the present invention is to improve the user experience in a dispensing environment.

Another object of the present invention is to allow simultaneous configuration of a plurality of dispensing devices disposed in an environment, in order to produce a dynamic predefined olfactory signature.

To this end, there is proposed a system for dispensing a liquid into an environment, this system comprising

- at least one dispensing device having a settable operating parameter and configured to dispense said liquid,
- a plurality of sensors comprising at least one air quality sensor,
- a control unit configured to gather a datum captured by at least one sensor of said plurality of sensors and to adjust, based on at least said captured datum, said operating parameter of said at least one dispensing device,
- said at least one air quality sensor incorporating a suction fan configured to suck air according to a settable direction, said at least one air quality sensor being configured to measure the quality of the sucked air,
- the control unit being configured to adjust said operating parameter based on at least the quality of the air sucked according to said settable direction.

Various additional features can be provided, alone or in combination:

- the air quality sensor is an odor sensor, a gas sensor, a particle sensor, or a bacteria sensor;
- said plurality of sensors further comprises an image sensor configured to capture an image which at least partially covers the environment;
- the control unit is configured to recognize an individual comprised in said image, the control unit being further configured to adjust said operating parameter based on at least the recognized individual;
- the control unit is configured to recognize an emotional state of an individual comprised in said image, the control unit being further configured to adjust said operating parameter based on at least the recognized emotional state;
- the control unit is configured to estimate a number of individuals comprised in said image, the control unit being further configured to adjust said operating parameter based on at least the estimated number of individuals;
- the image sensor is movable;
- the image sensor is carried by an unmanned aerial vehicle or by an electric rail vehicle;
- the dispensing device comprises a blower fan configured to push in a settable direction a gas flow produced by said dispensing device.

Other features and advantages of the invention will appear more clearly and in a concrete manner on reading the description of embodiments hereinafter, which is made with reference to the FIG. 1 which schematically illustrates a dispensing system according to various embodiments.

Referring to the unique FIGURE, there is schematically represented a dispensing system 1-9 configured to dispense one or several liquid(s) in an environment 10.

The environment 10 is any interior, semi-interior or exterior space incorporating one or several area(s) where at least one liquid is to be dispensed. This environment 10 is, for example,

- a point of sale with one or several floor(s) such as a pharmacy, a specialist store, a mini-market, a mega store, a supermarket, or even a hypermarket;
- a catering establishment incorporating, for example, a kitchen, a dining room, a smoking room, a non-smoking room, toilets, a terrace and/or a premise containing food products;
- a building complex such as a hospital center, a medical clinic, a spa center, a shopping center, a business center, a waste center, a henhouse, an industrial or agricultural production space, an airport, or a tourist, cultural, relaxation or leisure space such as a hotel or a cinema;
- individual or collective living area such as a private home, a living unit, or a retirement home.

By area, it should be understood here any space of the environment 10 such as an entrance, a room, a bedroom, a hall, a section, a corridor, a floor or part thereof.

The dispensing system comprises a plurality of dispensing devices 1-4 disposed in the environment 10. These dispensing devices have settable operating parameters. The dispensing system also comprises a control unit 5 configured to monitor the operation of the dispensing devices 1-4. These dispensing devices 1-4 are, under monitoring of the control unit 5, capable of dispensing into the atmosphere, in particular by nebulization, one or several liquid(s).

Each of the dispensing devices 1-4 is in fluid communication with one or several container(s) comprising, respectively, a liquid intended to be dispensed in one or several area(s) of the environment 10.

A liquid intended to be dispensed by nebulization in an area of the environment 10, separately or in combination with others, is, for example, a liquid with odoriferous power such as an interior perfume or an aromatic essence, water enriched with plants and/or vitamins, an essential oil, thermal water, an odor neutralizer, a medicated liquid, a deodorant, or a chemical solution with disinfectant, insecticidal, repellent, bacteriostatic, virucidal, or fungicide power.

More generally, the dispensing devices 14 transform a product, in particular active or aromatic liquid compounds, in dry volatile micro particles behaving, in the atmosphere of the environment 10, like a gas.

In one embodiment, at least one of the dispensing devices 1-4 is a nebuliser (in particular, with a venturi effect). This nebuliser comprises extraction means (such as an air compressor or an air pump) and a solenoid valve (or electrovalve) settable and controllable remotely by the control unit 5. The extraction means are capable of extracting a liquid from a container at a given settable flow rate and pressure. The nebuliser transforms the liquid to be dispensed into a mist of very fine droplets in the form of a gas flow which can be kept suspended in the atmosphere of the environment 10.

In another embodiment, a dispensing device 1-4 incorporates a blower fan configured to push/propel in a given settable direction the gas flow produced by this dispenser. This direction can be monitored by the control unit 5.

The dispensing system further comprises a plurality of sensors 6-9. These sensors 6-9 are arranged to measure or capture data intended to be used by the control unit 5. These data are exploited by the control unit 5 in order to adjust at least one operating parameter of the dispensing devices 1-4.

Said plurality of sensors 6-9 comprises at least one air quality sensor. This air quality sensor makes it possible to detect the presence of at least one predefined molecule or gas in the atmosphere of the environment 10 or an area thereof. In another embodiment, the air quality sensor determines the proportion of a predefined gas in the surrounding atmosphere.

For example, this air quality sensor is a device which makes it possible to change these physical properties following exposure to a predefined gas. Transforming this change into a measurable electrical signal provides information on the nature of the gases detected and possibly their concentrations. This air quality sensor is, for example, a metal oxide (MOX) based sensor, a polymer-based sensor, an optical sensor by infrared detection, or a carbon nanotube-based sensor.

More generally, the air quality sensor aims to measure the quality of the indoor air in the environment 10. For this purpose, at least one particle and/or a gas in the atmosphere of the environment 10 are observed by an air quality sensor. The gas to be detected is, for example, a toxic gas such as carbon dioxide (CO2), or carbon monoxide (CO), formaldehyde, and/or particles suspended in the air of a physical or biological nature. In another embodiment, the air quality sensor detects the presence or estimates the concentration in the ambient air of a predefined gas, of the carrier substance (such as water) of the active substance dispensed in the environment 10, and/or this same active substance.

As non-exhaustive examples, the air quality sensor is an odor sensor known in the state of the art by "electronic nose", a gas sensor, a particle sensor, a dust sensor, and/or a bacteria sensor.

In some embodiments, the air quality sensor continuously reads/captures a sample of the gas, at a predefined frequency, or at the request of the control unit 5.

The air quality sensor is separate from each of the dispensing devices 1-4. The air quality sensor is installed in a different location than that of the dispensing devices 1-4. In one embodiment, the air quality sensor is installed on a face opposite or, more generally, different from that of a dispensing device 1-4.

The air quality sensor comprises an suction fan. This air fan is configured to suck or draw air in a given direction towards the air quality sensor so that the latter can measure the quality of the air sucked in that direction. The direction of the suction fan fitted to the air quality sensor is, in one embodiment, settable and, preferably, controllable by the control unit 5. This suction fan can be directional, bidirectional or omnidirectional.

Advantageously, the air quality sensor equipped with a suction fan makes it possible to obtain measurements representative of the actual quality of the air in the area where this air quality sensor is installed.

Furthermore, by being provided with a suction fan, the air quality sensor can be installed in different places, including in particular confined or partially cloistered places (behind a partition out of sight or in a corner of a room for example), while being able to provide representative measurements (i.e. faithful to or close to reality) of the actual dispersion of a nebulized product or, more generally, of the air quality.

In order to cover large spaces, several air quality sensors, respectively, provided with one or several suction fan(s) may be considered. These air quality sensors may be disseminated in the environment 10 according to a predefined meshing (by floor, by room, by section, or by area, for example).

According to the data sent back by the air quality sensor(s) associated to an area of the environment 10, the control unit 5 adjusts at least one operating parameter of a corresponding dispensing device 1-4 (such as the liquid, the flow rate, the power and/or the direction of dispensing). It follows, advantageously, that depending on a desired result (such as a uniform and homogeneous distribution of the gas flow, focusing on a given direction or rather the exclusion of a certain direction), the control unit 5 adapts the control of the dispensing devices 1-4 (by acting, in particular, on the compressors, the solenoid valves, the orientation, and/or the blower fans of the dispensing devices 1-4).

Advantageously, by analyzing the data provided by an air quality sensor provided with a suction fan, the control unit 5 determines whether the quality of the air measured in a given direction/orientation of the suction fan is different from a desired value and consequently adjusts at least one operating parameter of the dispensing devices 1-4 associated beforehand to said direction of the suction fan. This direction indicates, for example,

- the source of a particular odor or gas (tobacco, frying, cooking, acidic odor, virus, fungi, bacteria, or germ for example) in order to focus the dispensing in that direction and allow faster neutralization of this smell;
- an axis of symmetry of an area (that of a corridor or a section for example), the direction of entry into an area or the direction of a place, an object or a target individual (such as a desk, a stand, a sofa or a seat for example) in order to favor dispensing in this direction;
- the boundary of an environmental area 10 or a sub-area to be excluded (for example, plants or food products sensitive to the nebulized liquid) in order to restrict the dispensing in that direction.

Advantageously, measurements performed by the air quality sensors of the air quality of the air sucked according to directions delimiting an area of the environment 10 make it possible to virtually limit the dispensing of the liquid in the atmosphere of this area. This makes it possible, for example, to locate the dispensing of a particular liquid in a target area of the environment 10 (a localized air treatment) such as a stand in a trade fair or a section in a store (an odorization by section).

Moreover, the deployment of a plurality of air quality sensors in the environment 10 makes it possible to maintain a predefined signature/imprint (olfactory, for example) of dispensing in this environment 10. This signature (or imprint) can be defined by the gas flow at different concentrations of one or several nebulized liquid(s) and cover one or several area(s) of the environment 10. Indeed, these air quality sensors, equipped with suction fans, make it possible to detect any modification in this signature so as to enable the control unit 5 to control the appropriate dispensing device(s) 1-4 to correct this change. A change of this signature may be due, for example, to temperature, humidity, the number of people present, a draught in the environment 10 or an area thereof, or the spread of a gas. A malfunction of a dispensing device 1-4, the exhaustion of a nebulized liquid and/or the apparition of an obstacle interposing between the air quality sensors and the dispensing devices 1-4 can also be at the origin of this modification. Consequently, the control unit 5 readjusts the operating parameters of the dispensing devices 1-4 (in particular, the flow rate, the power and/or the dispensing direction) in order to ensure the predefined signature of the gas flow in the space of the environment 10. In this case, the control unit 5 determines a reconfiguration for each dispensing device 1-4 concerned by the considered area of the environment 10 and, in real-time, controls this reconfiguration.

Also, the air quality sensors make it possible to determine whether the power of a dispensing device 1-4 is suitable for the dimensions of the area to be covered of the environment 10 (i.e. a dimensioning).

Moreover, the sensors 6-9 equipping the dispensing system also comprise at least one temperature and/or humidity sensor, enabling the control unit 5 to take into account, in control of the dispensing devices 1-4, the ambient temperature and/or the humidity of the air in the environment 10. The temperature and humidity of the air in the atmosphere of the environment 10 influence the propagation and the ability of the fine droplets to be in suspension and, consequently, their dispersion in the atmosphere of the environment 10.

The sensors 6-9 also comprise at least one image sensor (or visual sensor). This image sensor is, for example, a camera, a digital camera, a 2D/3D camera, or a 3D camera with depth detection making it possible to capture image data relating to an area of the environment 10. This image sensor allows the acquisition of still or video images integrating at least partially an area of the environment 10.

In one embodiment, one or several image sensor(s) are installed in an area of the environment 10 so as to allow the capture of at least one image of an individual within this area. This capture is aimed at the (visual) recognition of an individual comprised in these images, and/or the estimation of the number of individuals comprised in these images, and/or the recognition of an emotional state (i.e. mood such as joy, sadness, fear, disgust, a neutral state or anger for example) of an individual comprised in these images. In other embodiments, this image capture also aims to recognize the sex and/or age group of an individual comprised in acquired images.

Depending on the dimensions of the environment 10 and the extent of the field of view of the image sensor, several image sensors may be considered so that the count of the individuals present in the environment 10 and/or the recognition of one or more of these individuals and/or the mood of one or more of these individuals are close to the existing reality. Alternatively or in combination, at least one of the image sensors is movable. Indeed, this movable image sensor may be carried by an unmanned aerial vehicle (commonly called a "drone") or by an electric rail vehicle. An advantage of a movable image sensor is that it can cover a larger area of the environment 10.

In one embodiment, recognition of the emotional state of an individual present in an area of the environment 10 is estimated by the facial expression (an emotion sensor). The acquisition of successive images and/or images from several image sensors advantageously makes it possible to facilitate this recognition.

In another embodiment, an estimate of the number of individuals present in the environment 10 is obtained using a motion sensor configured to detect the displacement and/or the entry/exit of an individual in the environment 10 or in an area thereof. Alternatively or in combination, the motion sensor informs the control unit 5 of any detection of motion in its coverage area in order to order the capture of an image. In some embodiments, the image sensor and, possibly, an air quality sensor are coupled to one or several motion sensor(s), such that the detection of a motion in an area of the environment 10 automatically triggers the capture of one or several image(s) covering this area and the analysis of the air quality in this area. Thus, the control unit 5 can ask the image sensor for continuous or discontinuous acquisition for a predefined time correlated with the detection of motion by the motion sensor.

The control unit 5 is configured to recognize, from the data collected from the image sensors, the identity or the mood of a person present in the environment 10 and whose distinctive information have been registered in advance. For this purpose, the control unit 5 is provided with a database storing information relating to one or several individual(s) and/or moods established in advance. This information comprises, for example, one or several visual model(s) for each individual or mood. By visual model of an individual, it should be understood any distinct description based on descriptors and/or visual properties of an individual and/or mood.

Thus, a correlation can be measured between the image of an individual present in acquired images and prerecorded visual models in order to estimate the identity of this individual and/or his mood. This database further comprises metadata relating to predefined configurations of dispensing in the environment 10 associated with one or several profile(s). For this purpose, the control unit 5 comprises an image recognition application making it possible to extract, in the form of attributes for example, from the acquired images of the relevant parameters and to compare these parameters (using one of the various known image recognition algorithms) with information, previously memorized, relating to a list of individuals or emotional states. Following this comparison, the image recognition application determines, up to a determined confidence index, information (identity, and/or mood, and/or sex, and/or age group, for example) relating to an individual. Depending on the information determined, the control unit controls a configuration of the operating parameters associated with this information beforehand.

In one embodiment, the image recognition by the control unit 5 advantageously comprises a deep learning model or any other model based on an automatic learning method making it possible to recognize, with an index (or coefficient) of confidence, an individual, an emotional state of an individual and/or the number of individuals present in one or several acquired image(s). Indeed, images taken by the image sensors under various conditions (lighting, blackout, viewing angle for example) can be used to improve the performance of the image recognition application. This allows improving the ability to recognize and identify individuals and/or emotional states under different lighting conditions and with partial or complete images of individuals.

In another embodiment, the image recognition application implements convolutional neural networks capable of learning by themselves, from the acquired image data, distinctive information making it possible to estimate, by means of deep learning, information relating to an emotional state or to an individual comprised in the acquired images.

Moreover, the image recognition application applies, as it is known from the state of the art, face recognition algorithms, face detection and tracking algorithms and classification algorithms. This image processing may be carried out locally by the control unit 5 and/or remotely by means of a remote processing server to which the control unit 5 is connected.

Moreover, the dispensing system comprises a sensor of the level of the liquid to be nebulized (a level detector or a weight sensor) configured to measure the level of the liquid in a container. The control unit 4 monitors the level of the liquid and alerts the operator as soon as this level is below a predefined threshold.

The control unit 5 analyzes the data collected by sensors 6-9 and consequently adjusts at least one operating parameter of the dispensing devices 1-4. Indeed, according to the information gathered from the sensors 6-9, the control unit 5 determines an appropriate configuration of the dispensing devices 1-4 making it possible to achieve a target nebulization objective (making an olfactory imprint, treating a toxic substance or malodorous air, for example). The control unit 5 is then responsible for implementing this configuration.

In one embodiment, the determination by the control unit 5 of the operating parameters of the dispensing devices 1-4 takes into consideration, in addition to the information produced by the sensors 1-4 (air quality, image data), the previously determined operating parameters. The control unit 5 can indeed use the history of the operating parameters of the dispensing devices 1-4 to determine those to be controlled in response to information received from the sensors 6-9, or to anticipate a subsequent configuration of one or several dispensing device(s) 1-4.

The control unit 5 monitors (i.e. programs, commands, activates/deactivates or more generally modifies any settable operating parameter of a dispensing device) the dispensing devices 1-4 so as to select, according to the data provided by the sensors 6-9 and/or by an operator, the liquid to be dispensed, the flow 1*s* rate, the power, the frequency and the direction of nebulization.

The control unit 5 comprises at least one wireless or wired communications interface (via a local network for example) enabling its communication, directly or indirectly, with the dispensing devices 1-4, the sensors 6-9, a programming user terminal and/or a local or remote server. This server is, for example, a processing server, a Web server and/or a "Push" notification server. A wireless communication interface is, for example, a Bluetooth®, HomeRF®, ZigBee, Infra-red (IR), WiFi®, WiMax® interface, or an advanced universal network interface for terrestrial radio access (such as 3G, 4G or 5G for example).

In one embodiment, the control unit 5 can be operated by the user programming terminal (such as a computer, a tablet, or a smartphone) making it possible to intervene on the operation of the different modules of the dispensing system 1-9 and the implementation of a particular configuration of the dispensing system defined by an operator.

More generally, the control unit 5 is any hardware and/or software entity (of the type comprising a programmable logic controller or a processor, a memory, computer buses and various electronic components serving as a support for the execution of computing programs) capable of acquiring data and integrating functionalities allowing the implementation of a data processing method. The control unit 5 is, in one embodiment, a computerized management module, making it possible to manage several dispensing devices 1-4 deployed in the environment 10 based on data gathered from sensors 6-9 and/or provided by an operator.

In one embodiment, the control unit 5 notifies a user terminal (for example, a mobile application installed on a mobile terminal) of information/alerts concerning the dispensing system (level of the liquids in the containers, performance of the dispensing devices, the most/least used dispensing device, the data gathered from the sensors 6-9, confirming an individual determined with a confidence index below a predefined value, modification/addition of a profile of an individual to which is associated a nebulization signature).

The dispensing system according to the various embodiments described hereinabove is considered to be "smart" to the extent that the operating parameters of each of the dispensing devices 1-4 are automatically updated (automatic self-regulation) to ensure a predefined nebulization signature capable of varying over time and space. Thus, it is possible to create a dynamic olfactory ambience or a dynamic imprint such that a dispensing that follows an individual in his movement in the considered space and/or adapts to his emotional state.

In an illustrative implementation, the environment 10 is a house. The dispensing system comprises, in this case, at least one dispensing device capable of being connected to a plurality of containers. These containers comprise, respectively, a liquid intended to be nebulized. These containers are, for example, a first bottle containing a room fragrance, a second bottle containing an odor neutralizer, a third bottle containing a relaxing essential oil and a fourth bottle containing an essential oil to facilitate falling asleep. Depending on the identity of the individual and/or his mood and/or his age estimated by the control unit 5 from the image data gathered from at least one image sensor, the control unit 5 controls the connection of said at least one dispensing device to one of the aforementioned containers and adjusts its operating parameters (nebulization time, frequency, power, orientation of the blower fan, for example) in accordance with a predefined configuration. Depending on the measurements made by at least one air quality sensor, the control unit 5 readjusts at least one operating parameter of the dispensing devices so as to achieve a predefined imprint of the nebulized liquid. This imprint of the nebulized liquid varies in the space of the house (corridors, rooms, living room, bathroom, kitchen, toilets), overtime (time of day or day of the week for example) and according to data provided by sensors 6-9 (mood, individuals and/or air quality for example).

For example, if the individual's emotional state is "bored", the control unit controls the dispensing devices 1-4 so as to produce an ambience associated with this mood beforehand. In this respect, the third bottle is, in one embodiment, selected and at least one dispensing device is activated at predefined dispensing powers and directions. Of course, in view of the geometry of the room and the position in which the dispensing device is installed, this power can be variable depending on the direction of dispensing. The operating parameters of the dispensing device are readjusted according to the data sent back by one or several predefined air quality sensor(s). The detection of a predefined gas or odor triggers, for example, the use of the second bottle by another dispensing device or in place of the third cylinder until attenuation or neutralization of the detected gas or odor.

In another example, a dispensing signature (i.e. the container and/or the dispensing devices with their respective operating parameters) is determined based on user preferences previously informed to the control unit 5.

Advantageously, the servo-control described hereinabove results in a controlled dispensing in accordance with and adjusted to changes in the dispensing environment (volume, air quality, signature, occupancy, context, presence of individuals, emotional state).

Advantageously, the controlled dispensing system described hereinabove allows continuous and fine readjustment/setting of the dispensing devices in order to best approximate a predefined signature:

- automatically treats the ambient atmosphere according to the current context in that environment without requiring user intervention;
- allows, by means of air quality sensors, monitoring of the air quality in the atmosphere of the environment 10;
- allows, by means of image sensors, monitoring of the mood of an individual and/or the number of individuals present in this environment 10;
- improves the user experience in the environment 10;
- ensures a controlled distribution into a plurality of adjacent or remote areas of nebulized liquids in the atmosphere of the environment 10;
- adapts to the person and his environment (VIP, elderly, mood, time of day, for example);
- allows responding/reacting to scenarios that cannot be foreseen in advance by a predefined static dispensing program,
- allows, starting from a first arrangement of the dispensing devices within the environment 10, optimizing this arrangement with the effect of ensuring in the best way a predefined dispensing imprint.

Although the dispensing system is described hereinabove with respect to embodiments and variants, those skilled in the art will understand that these embodiments and variants are not restrictive and can be combined with each other and/or with any other equivalent embodiment.

The invention claimed is:

1. A system for dispensing a liquid in an environment, this system comprising at least one dispensing device having a settable operating parameter and configured to dispense said liquid, a plurality of sensors comprising at least one air quality sensor, a control unit configured to gather a datum captured by at least one sensor of said plurality of sensors and to adjust, based on at least said captured datum, said operating parameter of said at least one dispensing device, wherein said at least one air quality sensor incorporates a suction fan configured to suck air according to a settable direction, said at least one air quality sensor being configured to measure the quality of the sucked air, the control unit is configured to adjust said operating parameter based on at least the quality of the air sucked according to said settable direction.

2. The system according to claim 1, wherein the air quality sensor is an odor sensor, a gas sensor, a particle sensor, or a bacteria sensor.

3. The system according to claim 1, wherein said plurality of sensors further comprises an image sensor configured to capture an image which at least partially covers the environment.

4. The system according to claim 3, wherein the control unit is configured to recognize an individual comprised in said image, the control unit being further configured to adjust said operating parameter based on at least the recognized individual.

5. The system according to claim 3, wherein the control unit is configured to recognize an emotional state of an individual comprised in said image, the control unit being further configured to adjust said operating parameter based on at least the recognized emotional state.

6. The system according to claim 3, wherein the control unit is configured to estimate a number of individuals comprised in said image, the control unit being further configured to adjust said operating parameter based on at least the estimated number of individuals.

7. The system according to claim 3, wherein the image sensor is movable.

8. The system according to claim 7, further comprising an unmanned aerial vehicle or an electric rail vehicle, the image sensor being carried by the unmanned aerial vehicle or by the electric rail vehicle.

9. The system according to claim 1, wherein the dispensing device comprises a blower fan configured to push in a settable direction a gas flow produced by said dispensing device.

* * * * *